US00PP28771P3

(12) United States Plant Patent
Danziger

(10) Patent No.: US PP28,771 P3
(45) Date of Patent: Dec. 12, 2017

(54) ***NEMESIA* PLANT NAMED 'DNEMSANGEL'**

(50) Latin Name: ***Nemesia fruticans*×*Nemesia strumosa***
Varietal Denomination: DNEMSANGEL

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 36 days.

(21) Appl. No.: 14/999,426

(22) Filed: May 3, 2016

(65) Prior Publication Data

US 2017/0325390 P1 Nov. 9, 2017

(51) Int. Cl.
*A01H 5/02* (2006.01)

(52) U.S. Cl.
USPC ..... Plt./458

(58) Field of Classification Search
USPC ..... Plt./458
See application file for complete search history.

*Primary Examiner* — Susan McCormick Ewoldt
(74) *Attorney, Agent, or Firm* — Cassandra Bright

(57) ABSTRACT

A new and distinct *Nemesia* cultivar named 'DNEMSANGEL' is disclosed, characterized by an abundance of continuously flowering white flowers, fragrance, less fruit than normal for *Nemesia*, and good hot temperature tolerance. The new variety is a *Nemesia*, normally produced as an outdoor garden or container plant.

2 Drawing Sheets

Figure 1:
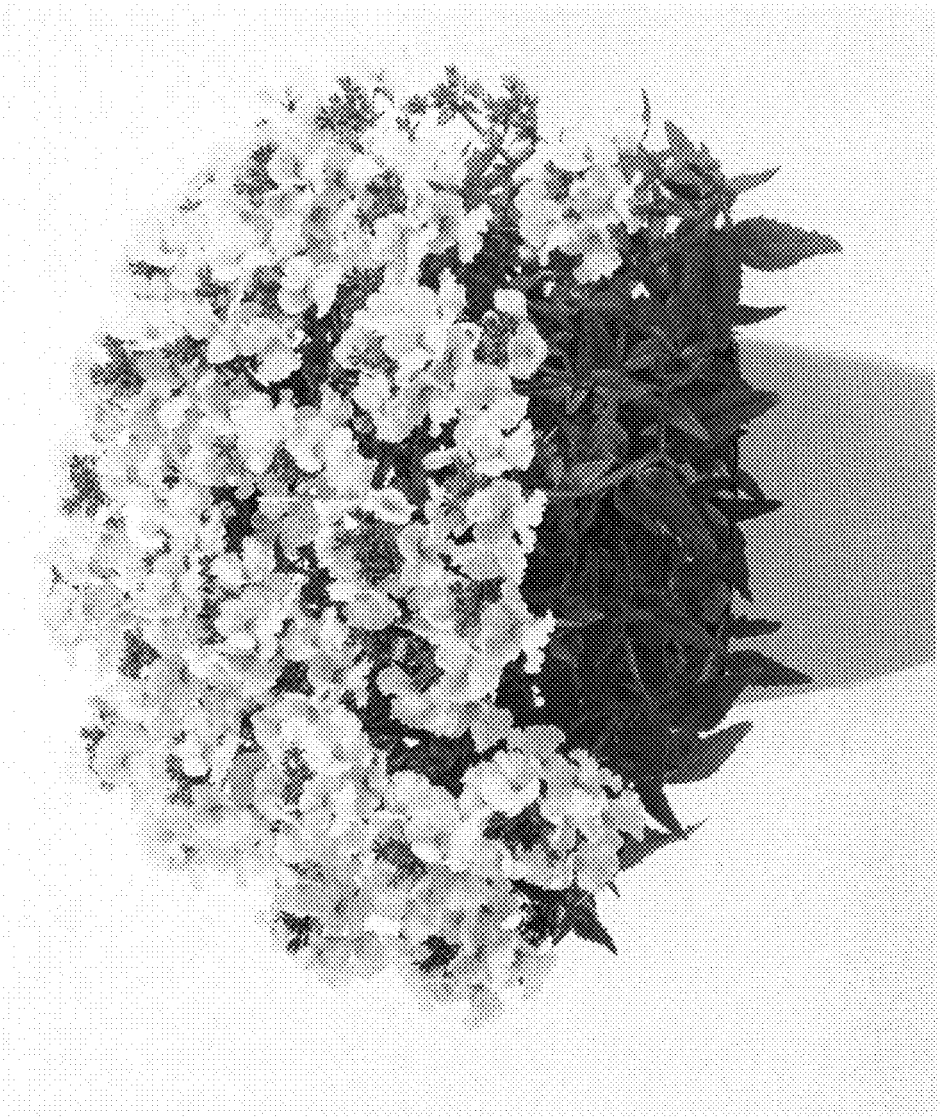

Latin name of the genus and species: *Nemesia fruticans*× *Nemesia strumosa.*

Variety denomination: 'DNEMSANGEL'.

BACKGROUND OF THE INVENTION

The new *Nemesia* cultivar is a product of a planned breeding program conducted by the inventor, Gavriel Danziger in Moshav Mishmar Hashiva, Israel. The objective of the breeding program was to produce new *Nemesia* varieties. The cross resulting in this new variety was made during June of 2011.

The seed parent is the, unpatented, propriety variety referred to as *Nemesia* 'NE-11-1911'. The pollen parent is the, unpatented, propriety variety referred to as *Nemesia* 'NE-11-3203'. The new variety was discovered in January of 2012 by the inventor in a group of seedlings resulting from the 2011 crossing, in a greenhouse in Moshav Mishmar Hashiva, Israel.

Asexual reproduction of the new cultivar 'DNEMSANGEL' first by vegetative cuttings was first performed during the January of 2013, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DNEMSANGEL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DNEMSANGEL' These characteristics in combination distinguish 'DNEMSANGEL' as a new and distinct *Nemesia* cultivar:

1 Fragrant flowers.
2. Abundance of white flowers.
3. Has less seed/fruit than most *Nemesia* varieties.
4. Exhibits good hot temperature tolerance.
5. Long, continuous flowering period.

PARENT COMPARISON

Plants of the new cultivar 'DNEMSANGEL' are similar to plants of the seed parent, *Nemesia* 'NE-11-1911' most horticultural characteristics, however, plants of the new cultivar 'DNEMSANGEL' differ in the following;

1. The new variety has white flowers, whereas the seed parent has red-orange flowers.
2. The new variety has fragrance, fragrance whereas the seed parent has no fragrance.
3. The new variety has larger flowers than the seed parent.

Plants of the new cultivar 'DNEMSANGEL' are similar to plants of the pollen parent, *Nemesia* 'NE-11-3203' most horticultural characteristics, however, plants of the new cultivar 'DNEMSANGEL' differ in the following;

1. The new variety has white flowers, whereas the pollen parent has red flowers.
2. The new variety has less fruit set than the seed parent.
3. The new variety has smaller flowers than the pollen parent.

COMMERCIAL COMPARISON

Plants of the new cultivar 'DNEMSANGEL' can be compared to the unpatented commercial variety *Nemesia* 'Angel Art Orange'. These varieties are similar in most horticultural characteristics; however, 'DNEMSANGEL' differs in the following:

1. Flower color of the comparator is orange, while flower color of the new variety is white.
2. The new variety has better cold temperature tolerance.

Plants of the new cultivar 'DNEMSANGEL' can also be compared to the unpatented commercial variety *Nemesia* 'Angel Art Almond'. These varieties are similar in most horticultural characteristics; however, 'DNEMSANGEL' differs in the following:

1. The new variety has fragrance, whereas the comparator has no fragrance.
2. The new variety has a darker yellow eye color than the comparator.
3. The new variety has smaller flower than the comparator.

BRIEF DESCRIPTION OF THE PHOTOGRAPHS

The accompanying photograph in FIG. 1 illustrates in full color a typical plant of 'DNEMSANGEL' grown in a greenhouse in Moshav Mishmar Hashiva, Israel.

Figure 2:
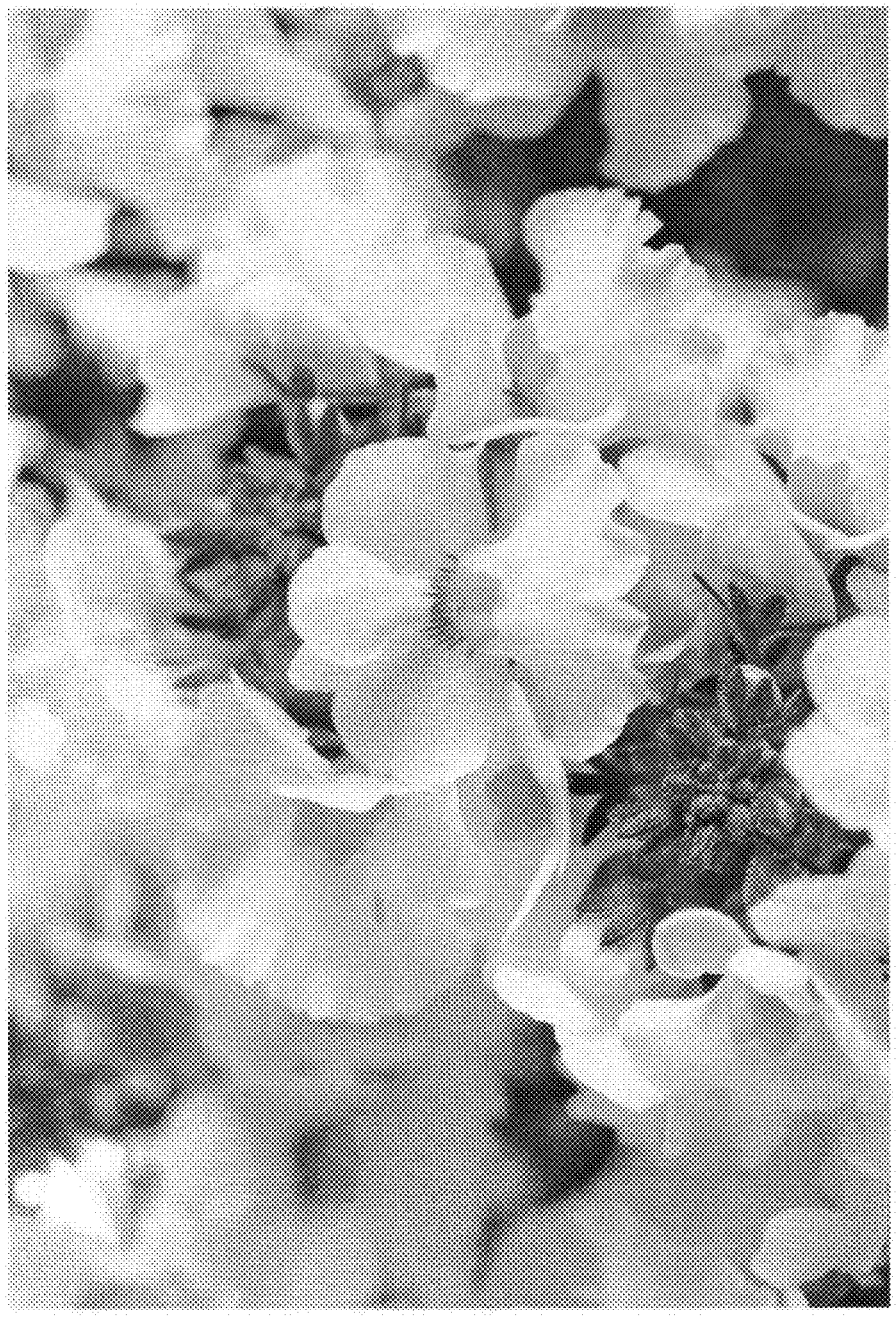

FIG. 2 illustrates in full color a typical flower of 'DNEMSANGEL'. Age of the plant photographed is approximately 8 weeks from a rooted cutting in a 12 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DNEMSANGEL' plants grown in a nursery in Moshav Mishmar Hashiva, Israel, under natural lighting. Measurements were taken during Autumn of 2015. The plants were approximately 78 days from a rooted cutting in a 12 cm pot. The growing temperature ranged from 17° C. to 24° C. during the days, 10° C. to 14° C. during the nights. Measurements and numerical values represent averages of typical plant types.

Botanical classification: *Nemesia fruticans*×*Nemesia strumosa* 'DNEMSANGEL'.

PROPAGATION

Time to initiate roots: 10-14 days.
Root description: Fibrous.

PLANT

Growth habit: Upright.
Pot size of plant described: 12 cm.
Height: To top of flowers: Approximately 15 cm.
Plant spread: 25 cm.
Growth rate: Fast.
Branching characteristics: Free branching.
Length of primary lateral branches: 14 cm.
Diameter of lateral branches: 0.4 cm.
Quantity of primary lateral branches: 5.
Characteristics of primary lateral branches:
- *Form*.—Quadrangular.
- *Diameter*.—0.3 cm.
- *Color*.—Near Yellow-Green 144B.
- *Texture*.—Smooth.
- *Strength*.—Flexible.

Internode length: 3.0 to 4.0 cm.

FOLIAGE

Leaf:
- *Arrangement*.—Opposite.
- *Quantity*.—Approximately 8 to 12 per branch.
- *Average length*.—5 cm.
- *Average width*.—2.5 cm.
- *Shape of blade*.—Lanceolate.
- *Apex*.—Broad acute.
- *Base*.—Attenuate.
- *Margin*.—Dentate.
- *Texture of top surface*.—Smooth.
- *Texture of bottom surface*.—Smooth.
- *Aspect*.—Flat.
- *Color*.—Young foliage upper side: Near Yellow-Green 144A. Young foliage under side: Near Yellow-Green 144C. Mature foliage upper side: Near Green N137B. Mature foliage under side: Near Yellow-Green 147C.
- *Venation*.—Type: Pinnate. Venation color upper side: Near Yellow-Green 144B. Venation color under side: Near Yellow-Green N144C.
- *Petiole*.—Absent.

FLOWER

Natural flowering season: Autumn, Winter, Spring under conditions in Moshav Mishmar Hashiva, Israel.
Days to flowering from rooted cutting: 21 days.
Inflorescence and flower type and habit: Raceme.
Rate of flower opening: 5 to 7 days from bud to fully opened flower.
Flower longevity on plant: 7 days.
Approximate quantity of flowers per plant: About 10 inflorescence per plant, each inflorescences has 5-8 flowers.
Persistent or self-cleaning: Self-cleaning.
Bud:
- *Shape*.—Obovate.
- *Length*.—0.3 to 0.5 cm.
- *Diameter*.—0.5 cm.
- *Color*.—Near Yellow-green RHS 146B.

Corolla:
- *Upper petals* (*upper lip*).—Number: 4. Length: Central petals: 14 mm. Lateral petals: 11 mm. Width: Central petals: 14 mm. Lateral petals: 9 mm. Shape: 4 petals fused in base. Angle of attachment: 45 degrees to stem. Margin: Entire. Texture: Smooth, all surfaces. Color: When opening: Upper surface: Near White N155C. Lower surface: Near White N155D. Fully opened: Upper surface: Near White N155B. Lower surface: Near White N155D.
- *Lower petal* (*lower lip*).—Length: 1.2 cm. Width: 2.3 cm. Shape: flabellate. Apex shape: rounded. Color: Upper surface: Near White 155C. Lower surface: Near White 155C.
- *Palate*.—Length: 3 mm. Width: 3 mm. Color: Near Yellow 17A. Texture: Smooth.
- *Throat*.—Length: 8 mm. Width: 4 mm. Texture: Pubescence. Pubescence: Puberulent.
- *Spur*.—Quantity: 1. Length: 3 mm. Diameter: 0.5 mm. Texture: pubescence. Color: Near Yellow-orange 22A.

Calyx:
*Form*.—Star-shaped with 5 sepals fused at the base.
*Length*.—5 mm.
*Diameter*.—9 mm.
*Sepal*.—Width: 1 mm. Shape: Ensiform. Apex: Acute. Margin: Entire. Texture: Pubescence. Color: Upper surface: Near Green N137 A. Lower surface: Near Green N137 B.
Pedicel:
*Strength*.—Flexible.
*Aspect*.—45 degree.
*Length*.—25-30 mm.
*Diameter*.—2 mm.
*Texture*.—Smooth.
*Color*.—Near Yellow-green 144 A.
Fragrance: Sweet, floral scent.

REPRODUCTIVE ORGANS

Stamens:
*Number* (*per flower*).—4.
*Filament length*.—0.2 cm.
*Anthers*.—Shape: oval. Length: 1 mm. Color: Near Yellow 5B.
Pollen:
*Color*.—Near Yellow 7 B.
*Amount*.—Abundant.
Pistils:
*Quantity per flower*.—1.
*Length*.—2 mm.
*Styles*.—Length: 1 mm. Color: Near Yellow-Green 148 B.
*Stigma*.—Shape: Oval. Color: Near Yellow-Green 148 B.

OTHER CHARACTERISTICS

Seeds and fruits: None observed.
Disease/pest resistance: Neither resistance nor susceptibility to normal diseases and pests of *Nemesia* has been observed.
Temperature tolerance: Tolerant to temperatures up to 28° C.

What is claimed is:
1. A new and distinct cultivar of *Nemesia* plant named 'DNEMSANGEL' as herein illustrated and described.

* * * * *